United States Patent [19]

Bryant et al.

[11] Patent Number: 5,163,029

[45] Date of Patent: Nov. 10, 1992

[54] METHOD FOR DETECTION OF INFLUX GAS INTO A MARINE RISER OF AN OIL OR GAS RIG

[75] Inventors: Thomas Bryant, Colebrook; Arthur Hay, Cheshire; Donald S. Grosso, West Hartford, all of Conn.

[73] Assignee: Teleco Oilfield Services Inc., Meriden, Conn.

[21] Appl. No.: 652,887

[22] Filed: Feb. 8, 1991

[51] Int. Cl.⁵ ............................................. G01V 1/36
[52] U.S. Cl. ...................................... 367/83; 73/155; 166/337; 175/48
[58] Field of Search ................ 367/25, 28, 30, 48, 367/81–86, 911, 912; 340/850, 853; 166/336, 337; 175/40, 48, 50; 73/155; 181/102

[56] References Cited

U.S. PATENT DOCUMENTS

| | | | |
|---|---|---|---|
| 2,232,476 | 2/1941 | Ritzmann | 175/40 |
| 2,560,911 | 7/1951 | Wolf | 181/102 |
| 2,573,390 | 10/1951 | Blanchard | 367/81 |
| 3,100,023 | 8/1963 | Clements | 175/40 |
| 3,100,994 | 8/1963 | Junger | 175/50 |
| 3,208,349 | 9/1965 | Burnett et al. | 175/40 |
| 3,316,997 | 5/1967 | McNog | 175/50 |
| 3,760,891 | 9/1973 | Gadbois | 175/48 |
| 3,821,726 | 6/1974 | Chang et al. | 175/48 |
| 3,865,201 | 2/1975 | Haden | 175/50 |
| 3,900,827 | 8/1975 | Lamel | 175/40 X |
| 3,906,435 | 9/1975 | Lamel et al. | 175/50 X |
| 3,910,110 | 10/1975 | Jefferies et al. | 73/155 |
| 3,961,308 | 6/1976 | Parker | 340/18 X |
| 4,147,222 | 4/1979 | Patten et al. | 175/9 |
| 4,273,212 | 6/1981 | Dorr et al. | 181/102 |
| 4,590,593 | 5/1986 | Rodney | 367/83 |
| 4,733,232 | 3/1988 | Grosso | 340/861 |
| 4,733,233 | 3/1988 | Grosso et al. | 340/861 |
| 4,964,085 | 10/1990 | Coope et al. | 367/35 |
| 5,006,845 | 4/1991 | Calcar et al. | 340/853 |

Primary Examiner—Brian S. Steinberger
Attorney, Agent, or Firm—Fishman, Dionne & Cantor

[57] ABSTRACT

In accordance with the present invention, several methods are presented for the detection of gas into an offshore marine riser (e.g., riser gas). In a first embodiment of this invention, an acoustic transmitter is positioned on or nearby the subsea blowout preventor stack and imparts continuous low frequency waves into the annular fluid in the marine riser. These imparted waves define pressure perturbations which are received by a pressure transducer positioned on the riser at a location above the acoustic transmitter. Gas detection in the riser is then indicated by determining the rate of change of certain characteristics of the output. The output characteristics are preferably the moduli and phase angles of the acoustic fundamentals and their harmonics. In a second embodiment of this invention, continuous or pulsed pressure waves are imparted into the marine riser using a transducer ring surrounding the riser comprised of piezoelectric or magnetostrictive elements which change shape when electrically stimulated. When such electrical stimulation occurs, preferably by a pulse containing multiple harmonics, the transducer rings impacts the riser pipe causing compressional waves to be set up in the annular fluid. The compressional waves are then sensed at or near the surface and changes in amplitude or phase shift are detected for determining the presence of influx gas.

19 Claims, 3 Drawing Sheets

METHOD FOR DETECTION OF INFLUX GAS INTO A MARINE RISER OF AN OIL OR GAS RIG

BACKGROUND OF THE INVENTION

The present invention relates to exploration for sources of hydrocarbon fuel and particularly to enhancing the safety of oil and gas well drilling procedures. More specifically, this invention is directed to apparatus and methods for detection of the infusion of gas into a borehole and especially to apparatus and methods for a gas infusion detection system which detects gas influx in the marine riser of an offshore drilling rig.

In the drilling of oil and gas wells, drilling safety and efficiency are extremely important. One safety problem relates to what is known as a "blowout". A zone of high geopressure, contained by cap rock, will occasionally be unknowingly encountered during drilling. If this pressure exceeds the hydrostatic pressure exerted by the drilling mud, and the formation has sufficient permeability to allow fluid flow, then the formation fluid will displace the drilling mud. This is referred to as a "kick"; and if unchecked will cause what is known as a "blowout" condition. One borehole condition which the driller desires to monitor, in order to ensure against "blowout" is gas influx.

Various techniques have previously been proposed, and in some cases implemented for measuring gas infusion into a borehole including sensing the borehole annulus pressure, sensing the pressure differential between the interior of the drill string and the annulus, measuring the velocity of sound in the drilling mud, measuring the resistivity of the drilling mud and various other tests based upon attempts to measure the pressure of the formation through which the drill string is penetrating or has penetrated. These previously proposed gas detection techniques, and particularly those based upon pressure measurements, all have deficiencies which severely limit their usefulness. An improved borehole fluid influx detection system is described in U.S. Pat. Nos. 4,733,232 and 4,733,233, both of which are assigned to the assignee hereof and incorporated herein by reference. In accordance with the methods of these prior patents, the pressure in the annulus between the standpipe (drill pipe or string) and wall of the well is monitored at the surface. Frequency or amplitude modulation of the mud flow in the standpipe by a coherent energy source at a point near the drill bit will result in the mud flow in the annulus containing information in the form of reflections of the modulation of the flow in the standpipe. Pressure monitoring of the mud flow in the annulus at the surface thus results in the detection of the reflected information resulting from modulation of the column of drilling mud in the drill string (standpipe). The pressure variations detected in the annulus are compared to pressure variations detected in the standpipe. A significant change in phase and/or amplitude ratio between the standpipe and annulus pressure variations, particularly a change in phase and/or amplitude ratio which constitutes a significant deviation from a previously established history, will indicate that there is a fluid influx into the annulus since fluid, for example gas, flowing into the drilling mud will produce attenuation of the modulated information and/or will affect the transmission velocity.

While well suited for its intended purposes, the method of U.S. Pat. Nos. 4,733,232 and 4,733,233 is not adapted for measuring gas influx (e.g. riser gas) when no drill string is present in the borehole. This is a particularly serious problem in offshore oil rigs where there is a need to measure gas influx whether a drill string is present in the borehole or has been withdrawn.

SUMMARY OF THE INVENTION

The above-discussed and other problems and deficiencies of the prior art are overcome or alleviated by the methods of detecting gas influx of the present invention. In accordance with the present invention several methods are presented for the detection of gas into an offshore marine riser (e.g., riser gas).

In a first embodiment of this invention, an acoustic transmitter is positioned on or nearby the subsea blowout preventor stack and imparts continuous low frequency waves into the annular fluid in the marine riser. These imparted waves define pressure perturbations which are received by a pressure transducer positioned on the riser at a location above the acoustic transmitter. Gas detection in the riser is then indicated by determining the rate of change of certain characteristics of the output. The output characteristics are preferably the moduli and phase angles of the acoustic fundamentals and their harmonics. The rate of change is initially determined from either a gas-free reference or from a suitable algorithm. Upon an indication of gas influx into the marine riser, a signal is delivered to surface instrumention actuating an alarm.

In a second embodiment of this invention, continuous or pulsed pressure waves are imparted into the marine riser using a transducer ring surrounding the riser comprised of piezoelectric or magnetostrictive elements which change shape when electrically stimulated. When such electrical stimulation occurs, preferably by a pulse (or thump) containing multiple harmonics, the transducer rings impacts the riser pipe causing compressional waves to be set up in the annular fluid. The compressional waves are both then sensed at or near the surface and changes in amplitude or phase shift are detected for determining the presence of influx gas as described in U.S. Pat. Nos. 4,733,232 and 4,733,233.

The above discussed and other features and advantages of the present invention will be appreciated and understood by those skilled in the art from the following detailed description of the drawings.

BRIEF DESCRIPTION OF THE DRAWINGS

Referring now to the drawings, wherein like elements are numbered alike in the several FIGURES.

DESCRIPTION OF THE PREFERRED EMBODIMENT

Figure 1:
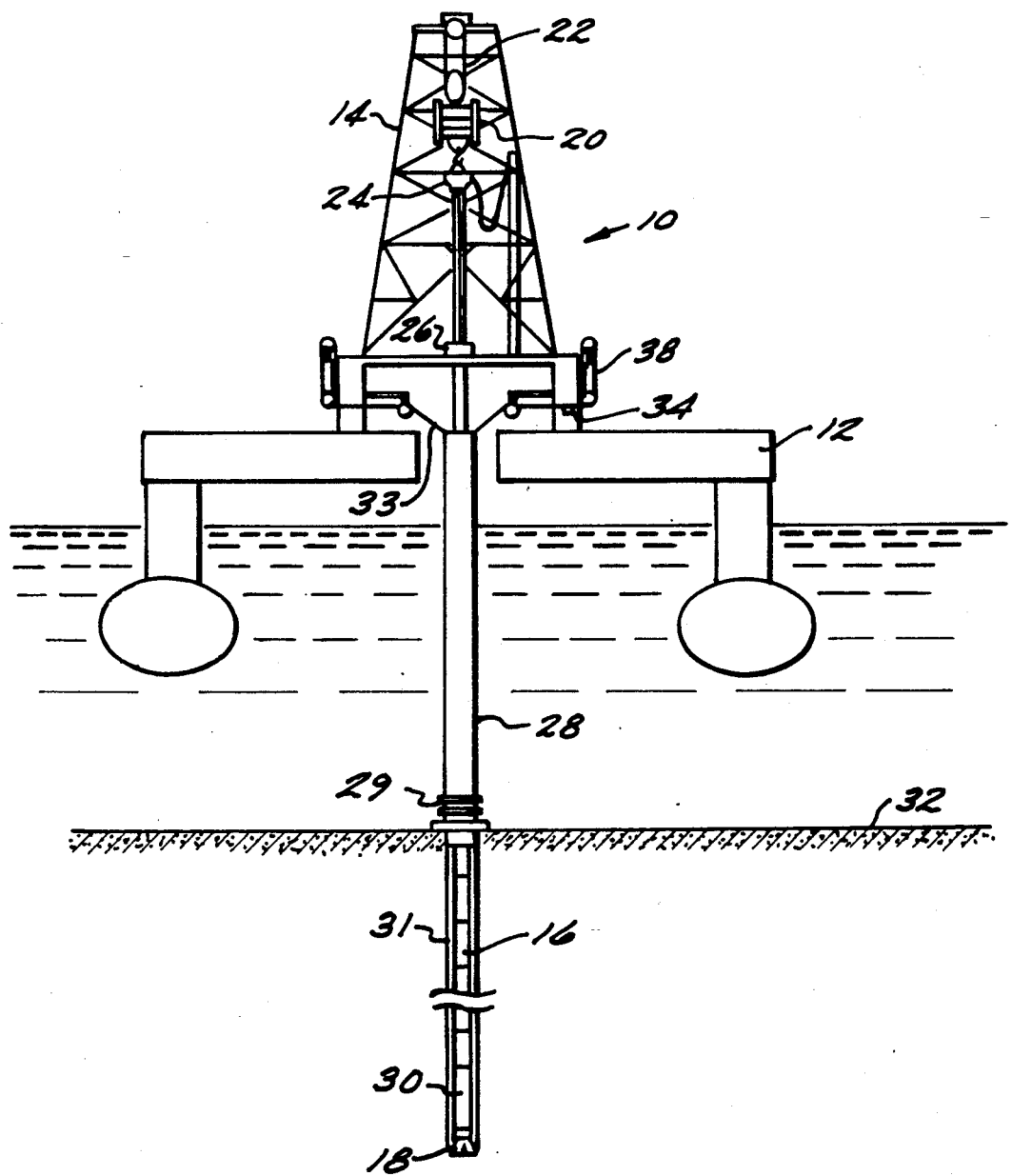
FIG. 1 is a diagrammatic side view of a floating drill rig and drill string assembly.

Referring first to FIG. 1, a well known floating drilling rig is shown generally at 10. Rig 10 comprises a floating drilling platform 12 having a derrick 14 supported thereon. Derrick 14 supports a drill string or drill stem 16 which terminates in a drill bit 18. As is well known in the art, the entire drill string may rotate, or the drill string may be maintained stationary and only the drill bit rotated (either of which may be the environment of the present invention). The drill string 16 is made up of a series of interconnected segments, with new segments being added as the depth of the well increases. The drill string is suspended from a movable or travelling block 20 of a winch system 22, and the entire drill string may be driven in rotation by a square kelly 24 which slidably passes through but is rotatably driven by the rotary table 26 at the foot of the derrick. A motor assembly (not shown) is connected to operate both winch 22 and rotatably drive rotary table 26. A drilling riser 28 comprises a conduit which is annularly arranged about drill string 16. Riser 28 is fixed in place by direct attachment to a well head 29 which is secured to sea floor 32.

The lower part of drill string 16 may contain one or more segments of larger diameter and thicker walls (e.g., bottom hole assembly 30) than other segments of the drill string (known as drill collars). As is well known in the art, bottom hole assembly 30 may contain sensors and electronic circuitry for sensors and power sources, such as mud driven turbines which drive drill bits and/or generators and, to supply the electrical energy for the sensing elements. Drill cuttings produced by the operation of drill bit 18 are carried away by a mud stream rising up through the free annular space 31 between the drill string and the wall of the well. The mud column in drill string 16 may serve as the transmission medium for carrying signals of downhole parameters to the surface. This signal transmission is accomplished by the well known technique of mud pulse generation whereby pressure pulses are generated in the mud column in drill string 16 representative of sensed parameters down the well. The drilling parameters are sensed in a sensor unit in bottom hole assembly 30 near or adjacent to drill bit 18. Pressure pulses are established in the mud stream within drill string 16, and these pressure pulses are received by a pressure transducer and then transmitted to a signal receiving unit which may record, display and/or perform computations on the signals to provide information on various conditions down the well. A heave compensation system comprised of rucker lines 33, riser tensioners 38 and compensated traveling block 20 is also shown in FIG. 1.

Figure 2:
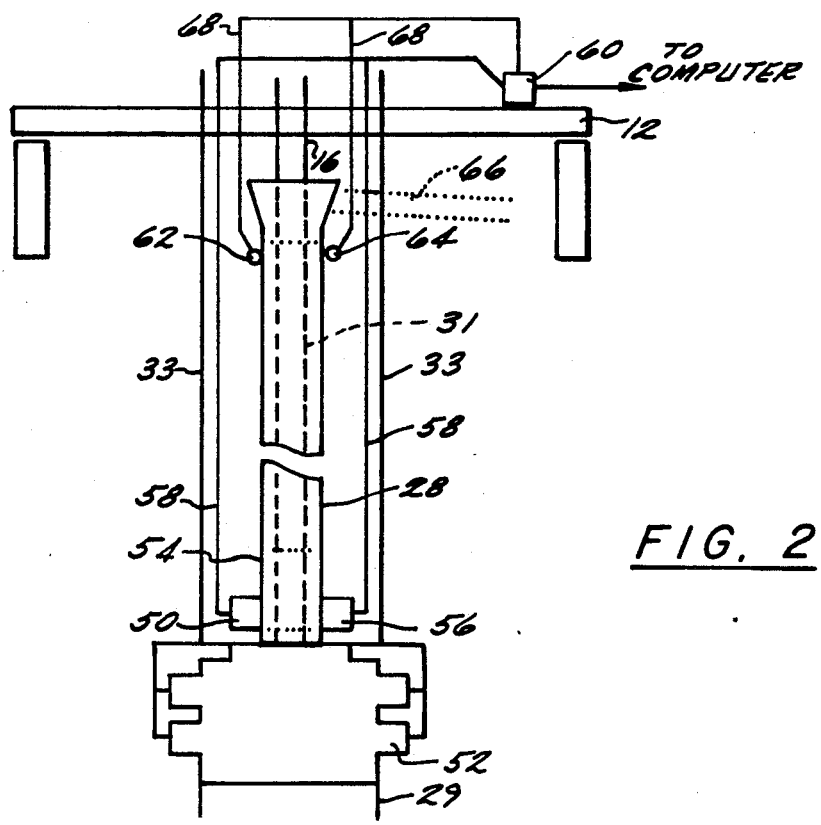
FIG. 2 is a diagrammatic side view of a riser gas influx detector assembly in accordance with a first embodiment of the present invention.

Referring now to FIG. 2, a method or detection of the entry of gas into a marine riser in accordance with a first embodiment of the present invention will now be described. In accordance with this embodiment of the present invention, an acoustic transmitter 50 is positioned on riser 28 at a location above the sub sea blowout preventor stack 52. Preferably, acoustic transmitter 50 comprises a small, rugged and robust pump and is located on a complimentary instrumented joint 54 of riser 28, with this joint 54 being inserted just above the lower riser latching joint. In a preferred embodiment, a second acoustic transmitter unit 56 is also provided on riser 28 at a location opposed from acoustic transmitter 50. Both transmitting units 50 and 56 are hardwired via cable 58 to a surface power and control unit 60. A pressure transducer 62 is positioned on riser 28 at a location above transmitter 50. In addition, and in a preferred embodiment, a second pressure transducer 64 is positioned above transmitter 56. It will be appreciated that both pressure transducers 62 and 64 are positioned below the flow line 66 of the drilling fluid.

When acoustic transmitters 50 and 56 are actuated, the transmitters will generate a continuous repetitive multi-frequency acoustic wave (preferably a square wave). These acoustic waves will both travel upwardly through the annulus 31 (between the drill pipe 16 and riser 28) directly to transducers 62 and 64 and the waves will travel downwardly to the bottom of the hole (see FIG. 1) where they will be reflected and then travel upwardly in the annulus 31 to receivers 62 and 64. Accordingly, the acoustic waves which travel directly up through the annulus to pressure transducers 62, 64 will be defined hereinafter as the first arrival waves while the acoustic waves which initially travel downwardly through the annulus and then are reflected back upwardly through the annulus to transducers 62, 64 will be defined hereinafter as the second arrival waves. As will be discussed hereinafter, the direct or first arrival waves will provide the primary means for detection of gas entry into riser 28. The indirect or secondary waves constitute a secondary means for detection of gas entry into the rise with the secondary waves sampling the annular drilling fluid located between the transmitter position and the bottom of the well bore.

There are presently three variations related to deployment of the transmitters and receivers in accordance with the first embodiment of this invention. The first variation is depicted in FIG. 2. In this first variation, the acoustic waves travel up riser 28 within the annular fluid 31 at a speed related to the speed of sound through a fluid medium of the same density as the drilling fluid. These waves are detected by the pressure sensitive receivers 62, 64 located within a joint of riser 28. In this first variation, the pressure transducers 62, 64 are located in a joint of riser 28 near its surface outlet, but below the flow line exit 66 for the drilling fluid. These pressure transducers 62, 64 are also hard wired to a surface power control unit 60 via hardwiring 68. The pressure pertubations created by acoustic transmitters 50, 56 are continually monitored via a signal transmission to a computerized data acquisition and processing unit on the surface.

Figure 3:
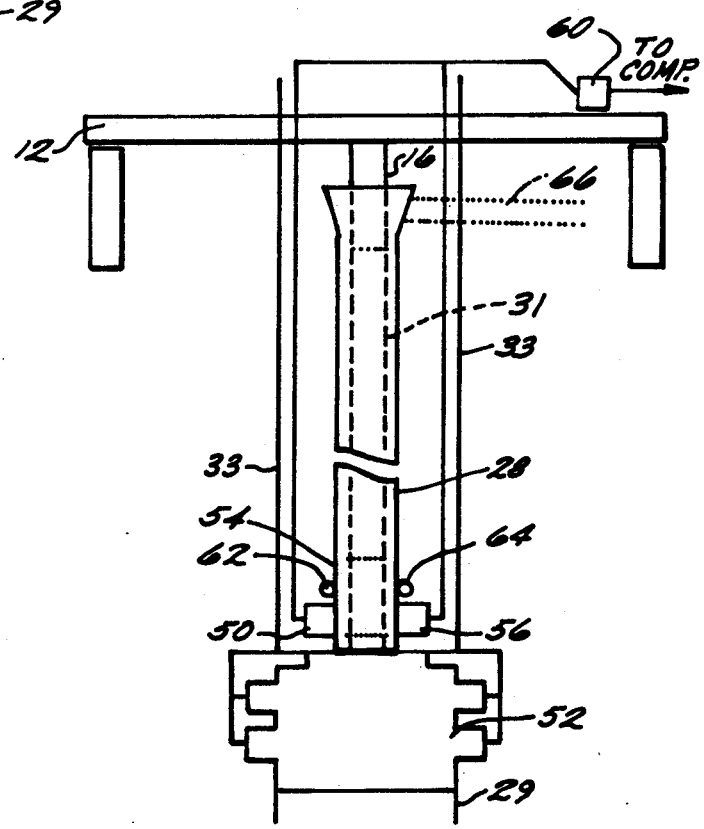
FIG. 3 is a diagrammatic view, similar to FIG. 2, of a variation of the first embodiment of this invention.

In another variation of the first embodiment of this invention shown in FIG. 3, the acoustic receivers 62, 64 are located in the same specially instrumented riser joint as the transmitters 50, 56 at a distance of two to twenty feet above transmitters 50, 56. The direct acoustic wave detected by receivers 62, 64 are then transmitted via a hard wire connection 58 to the service control unit 60.

Figure 4:
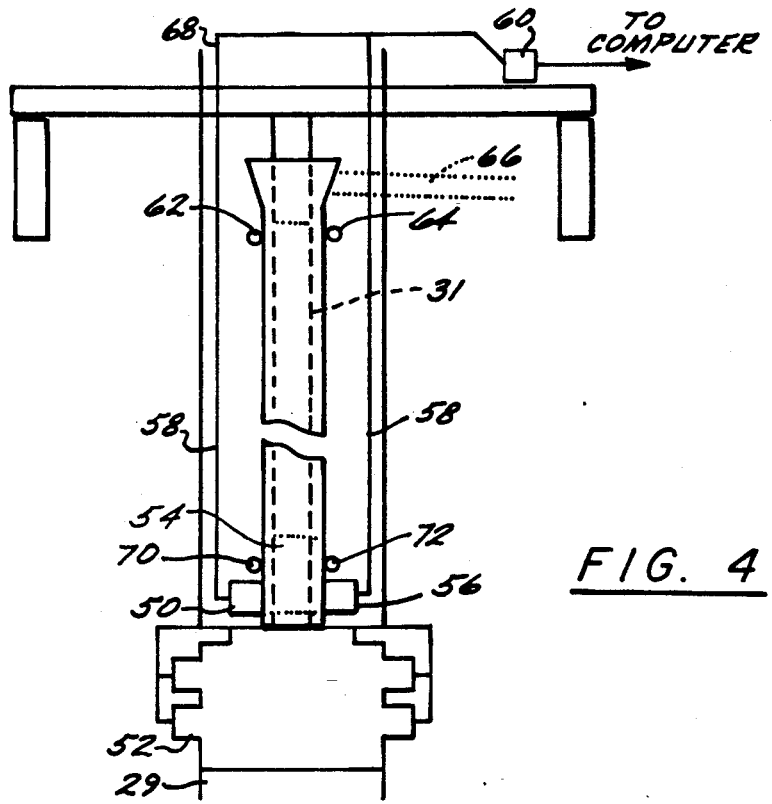
FIG. 4 is a diagrammatic view, similar to FIG. 2, of still another variation of the first embodiment of this invention.

In still another variation of the first embodiment of this invention shown in FIG. 4, the acoustic receivers 62, 64 are mounted into a specially instrumented riser joint that is located a considerable distance above a second acoustic receiver 70. Receiver 70 (and its redundant twin 72) are located on the same specially instrumented riser joint containing transmitters 50, 56. In this latter variation, the receivers 62, 64 (i.e. located closest to the surface) may be dedicated to servicing the direct signal with the receivers 72, 74 (i.e. located in the same joint as transmitters 50, 56) being used to detect the first arrival waves, the second arrival waves or a signal originating from another source such as an MWD pulser.

In all of the above discussed variations of the first embodiment, the acoustic pressure pertubations are continually monitored from the one or more acoustic receivers. These monitored pressure pertubations are acquired and processed by a computer system that includes a Fourier Transform algorithm. Application of the Fourier Transform algorithm will reveal the amplitudes of both moduli and phase angle for the fundamental and harmonic frequencies of the signal created by the transmitters.

In the case of a single receiver located at or near the surface (i.e., the FIG. 2 embodiment), the detection method of this invention may be employed using only the information provided by this receiver. This information represents the measured output. Characteristics of the input are known with respect to frequency but are estimated with respect to moduli and phase angles. The detection process in this case involves an algorithm relating the frequency dependent values of modulus and phase angle of the output.

In the case of there being two receivers (i.e., the FIG. 4 embodiment), one located near the transmitter and the other near the surface, information received by the near surface receiver (the output) may be referenced to information provided by the former receiver (the input). In this case, the detection process may resemble that of the first case but may additionally include a comparison to gas free historical values.

The amount of gas in the drilling fluid may be determined qualitatively or quantitatively. Qualitatively, the amount of gas may be related by the degree of change in the frequency dependency values of moduli and phase angles. For relatively small concentration of gas, only the moduli and phase angles of the higher harmonics are affected. As the amount of gas increases, changes in these values increases, and the same properties of lower harmonics and fundamentals are similarly affected. Quantitatively, the concentration of gas may be determined by its influence on the speed of sound within the annular drilling fluid. This speed is proportional to the gas fluid mixture. This speed may be determined by measuring the time delay between input transmission and output reception.

Figure 5:
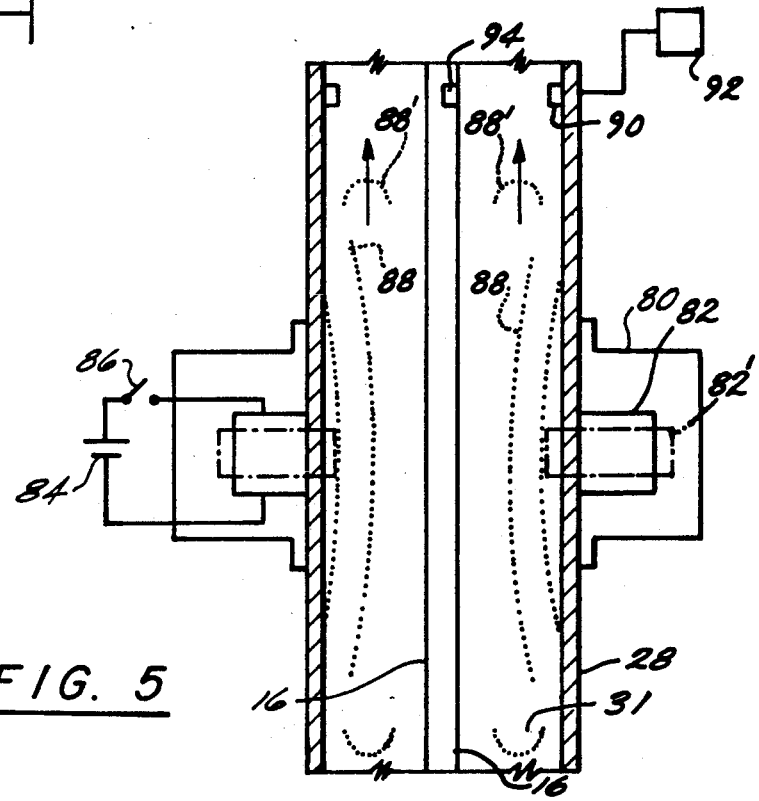
FIG. 5 is a diagrammatic side view of a riser gas influx detector assembly in accordance with a second embodiment of the present invention.

Turning now to FIG. 5, a second embodiment of the present invention will now be described. As in the first embodiment, in the second embodiment, a transmitter is used to impart energy into the annular fluid 31 between the drill pipe 16 and riser 28. However, in the second embodiment, the acoustic transmitter comprises a transducer ring 80 which is attached to and surrounds an exterior wall of riser 28. Preferably, transducer ring 80 is located just above the sub sea blowout preventor stack. Transducer ring 80 preferably comprises piezoelectric or magnetostrictive elements that change shape when electrically stimulated as illustrated by the solid and dashed lines in FIG. 5. Thus, the ring depicted at 82 is shown prior to electrical stimulation while the flattened ring depicted at 82' is shown after stimulation by a power source 84 which has stimulated ring 82' upon actuation of an appropriate switch shown schematically at 86. When excited, preferably by an electrical pulse containing multiple harmonics, ring 82 will impact or thump the riser pipe 28 causing compressional waves to be set up in the annular fluid 31. The coupling of this energy depends on the transfer impedance between the riser pipe wall/annular fluid interface and the annular fluid. This couple is a function of the gas content of the local annular fluid. These compressional waves indicated at 88 will radiate outwardly with some of the energy going towards the surface (shown at 88' and passing through the length of riser 28). Some energy will go down the well and reflect back up from the bottom and then to transducers 90 and 94. Additionally, the compressional waves will be affected by the presence of annular gas as the wave travels to the surface. The affect of annular gas on acoustic waves is more fully described in U.S. Pat. Nos. 4,733,232 and 4,733,233. If sufficient energy and heat exchange is available, then the waves transmitted by annular ring 82 may be a sine wave (continuous or pulse) or a sine sweep. Alternatively, the wave shape could be tailored (e.g. square trapezoid, triangular) to optimize the input energy and/or the gas detection.

As in the aforementioned U.S. Patents, the compressional waves 88' are detected at or near the surface by a suitable pressure tranducer 90 and examined by a computer 92 for the effects of gas (e.g. a change of amplitude or phase shift). In addition to a transducer being located in the annulus (at 90) such as a pressure transducer for detecting the compressional waves directly, an additional transducer 94 may be positioned within drill pipe 16 or in the standpipe 29 for detecting compressional waves which have been coupled into the drill pipe fluid. The use of these two detectors 90 and 94 will double the effect of the coupling impedance affected by the gas. Alternatively, the measurement by receivers 90 and 94 may be a combination thereof.

The present invention provides many features and advantages and provides an effective means for the detection of gas entering a marine riser. Significantly, the present invention allows the detection of gas influx into the riser in the absence of annular fluid circulation created by the action of the large reciprocating pumps typically used to circulate drilling fluid. Hence, detection of gas entry into the riser may take place while drill pipe is being run into, or pulled out of, the riser and well bore. Detection of gas influx may also take place when no drill string is present in the hole. This is a distinct advantage to the method of U.S. Pat. Nos. 4,733,232 and 4,733,233. In addition, the detection process may also occur during periods of circulation. In this latter situation, use of the present invention for gas influx detection may take place concomitantly with the use of a gas influx detection method such as that described in the foregoing U.S. patents.

While both gas influx detection methods of the first and second embodiments provide equally good results, it will be appreciated that the second embodiment has a further advantage of being mounted on riser 28 without riser 28 requiring pipe modification, that is, riser 28 does not necessitate cuts or intrusions into the annulus as would the detection method of the first embodiment.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method of determining gas influx in a riser connected between a drill rig and the floor of a body of water, the riser normally surrounding a drill string in a borehole with an annular space being defined between the riser and the drill string, the annular space providing an annular channel for the flow of drilling fluid, and a blowout preventor stack on the riser adjacent the floor of the body of water, the method comprising the steps of:

positioning said transmitter means adjacent to and above said blowout preventor stack;

imparting energy waves from a transmitter means positioned on the riser to the drilling fluid in the annular space;

sensing the energy waves at a location above the transmitter using receiver means with said second energy waves comprising energy waves traveling directly between said transmitter means and said receiver means;

evaluating the sensed energy waves and determining the rate of change of at least one output characteristic of the energy waves; and determining gas influx in the riser based on the determined rate of change, said step of determining gas influx being irregardless of whether the drill string is positioned in the borehole or whether drilling fluid is being circulated in the annular channel.

2. The method of claim 1 wherein:
said transmitter means comprises an acoustic transmitter.

3. The method of claim 2 wherein:
said acoustic transmitter comprises a pump.

4. The method of claim 1 including:
positioning said receiver means on said riser adjacent to and above said transmitter means.

5. The method of claim 1 wherein drilling fluid exits the annular space at a flowline on the drill rig and including:
positioning said receiver means below and near the flowline.

6. The method of claim 1 wherein said receiver means includes at least a first receiver and a second receiver spaced from the first receiver and wherein drilling fluid exists the annular space at a flowline on the drill rig and including:
positioning said first receiver on said riser adjacent to and above said transmitter means; and
positioning said second receiver below and near the flowline.

7. The method of claim 1 wherein:
said receiver means comprises pressure transducer means.

8. The method of claim 1 wherein:
said energy wave comprises continuous low frequency waves.

9. The method of claim 8 wherein:
said energy waves comprise sine waves.

10. The method of claim 1 wherein said energy waves have acoustic fundamentals and harmonics of said acoustic fundamentals and wherein said acoustic fundamentals and harmonics include moduli and phase angle and wherein said output characteristic comprises:
at least one of the moduli and phase angles of the energy waves' acoustic fundamentals and harmonics.

11. The method of claim 1 wherein:
said transmitter means imparts compressional waves into said riser.

12. The method of claim 11 wherein:
said transmitter means comprises transducer ring means surrounding said riser, said transducer ring means imparting said compressional waves into said riser.

13. The method of claim 12 wherein:
said transducer ring means comprises magnetostrictive elements which change shape upon electrical stimulation.

14. The method of claim 1 wherein said evaluating step also includes:
evaluating energy waves traveling initially downwardly from said transmitter means to the bottom of the borehole and then being reflected back upwardly to said receiver means in addition to the energy waves traveling directly between said transmitter means and said receiver means.

15. The method of claim 12 wherein:
said transducer ring comprises piezoelectric elements which change shape upon electrical stimulation.

16. A method of determining gas influx in a riser connected between a drill rig and the floor of a body of water, the riser normally surrounding a drill string in a borehole with an annular space being defined between the riser and the drill string, the annular space providing an annular channel for the flow of drilling fluid, and a blowout preventor stack on said riser adjacent the floor of the body of water, the method comprising the steps of:

positioning said transmitter means adjacent to and above said blowout preventor stack;

imparting energy waves from a transmitter means positioned on the riser to the drilling fluid in the annular space;

sensing the energy waves at a location above the transmitter using receiver means with said sensed energy waves comprising energy waves traveling initially downwardly from said transmitter means to the bottom of the borehole and then being reflected back upwardly to said receiver means;

evaluating the sensed energy waves and determining the rate of change of at least one output characteristic of the energy waves; and determining gas influx in the riser based on the determined rate of change, said step of determining gas influx being irregardless of whether the drill string is positioned in the borehole or whether drilling fluid is being circulated in the annular channel.

17. The method of claim 16 including:
positioning said receiver means on said riser adjacent to and above said transmitter means.

18. The method of claim 16 wherein drilling fluid exits the annular space at a flowline on the drill rig and including:
positioning said receiver means below and near the flowline.

19. The method of claim 16 wherein said receiver means includes at least a first receiver and a second receiver spaced from the first receiver and wherein drilling fluid exits the annular space at a flowline on the drill rig and including:
positioning said first receiver on said riser adjacent to and above said transmitter means; and
positioning said second receiver below and near the flowline.

* * * * *